(12) United States Patent
Tamura et al.

(10) Patent No.: US 6,620,104 B2
(45) Date of Patent: Sep. 16, 2003

(54) VITAL SIGNAL DETECTING APPARATUS AND NONINVASIVE BLOOD PRESSURE METER

(75) Inventors: Shinichi Tamura, Tajimi (JP); Naoki Fukaya, Obu (JP)

(73) Assignee: Denso Corporation, Kariya (JP)

( * ) Notice: Subject to any disclaimer, the term of this patent is extended or adjusted under 35 U.S.C. 154(b) by 451 days.

(21) Appl. No.: 09/745,839

(22) Filed: Dec. 26, 2000

(65) Prior Publication Data

US 2001/0016691 A1 Aug. 23, 2001

(30) Foreign Application Priority Data

Dec. 27, 1999 (JP) .......................... 11-368751
Sep. 6, 2000 (JP) ........................ 2000-270294

(51) Int. Cl.⁷ ............................................... A61B 5/00
(52) U.S. Cl. ...................... 600/485; 600/492; 600/502; 600/500
(58) Field of Search ................. 600/485, 492, 600/500–502, 503, 484, 507, 455, 441–449

(56) References Cited

U.S. PATENT DOCUMENTS

| 5,099,852 | A | * | 3/1992 | Meister et al. | ............... | 128/672 |
| 5,289,823 | A | * | 3/1994 | Eckerle | ....................... | 128/679 |
| 5,795,300 | A | * | 8/1998 | Bryars | ......................... | 600/500 |
| 6,331,162 | B1 | * | 12/2001 | Mitchell | ..................... | 600/485 |
| 6,447,456 | B1 | * | 9/2002 | Tsubata | ....................... | 600/455 |

FOREIGN PATENT DOCUMENTS

| JP | 5-7558 | 1/1993 |
| JP | 5-154136 | 6/1993 |
| JP | 5-184547 | 7/1993 |
| JP | 5-207978 | 8/1993 |
| JP | 7-327940 | 12/1995 |
| JP | 2664983 | 6/1997 |

\* cited by examiner

Primary Examiner—Mark Paschall
(74) Attorney, Agent, or Firm—Harness, Dickey & Pierce, PLC

(57) ABSTRACT

A vital signal detecting apparatus is composed of sensors for detecting pulse waves, an A/D converter for converting analog signals, corresponding to the pulse waves and derived from the sensors, into digital signals, a separation matrix calculation means, and a signal separation calculation circuit. The separation matrix calculation circuit calculates a separation matrix for separating an outer disturbance caused by body movement from the pulse waves. The signal separation calculation means divides the digital signals converted by the A/D converter into a vital signal containing no outer disturbance and a body movement signal indicating the outer disturbance by using the separation matrix.

19 Claims, 5 Drawing Sheets

VITAL SIGNAL DETECTING APPARATUS AND NONINVASIVE BLOOD PRESSURE METER

CROSS REFERENCE TO RELATED APPLICATIONS

This application is based upon and claims the benefit of Japanese Patent Applications No. 11-368751 filed on Dec. 27, 1999, and No. 2000-270294 filed on Sep. 6, 2000, the contents of which are incorporated herein by reference.

BACKGROUND OF THE INVENTION

1. Field of the Invention

The present invention is related to a vital signal detecting apparatus capable of detecting a vital signal containing no outer disturbance from pulse waves, and also related to a noninvasive blood pressure meter adopting a system for measuring a variation in blood pressure.

2. Description of the Related Art

Conventionally, such blood pressure meters capable of continuously measuring blood pressure with employment of cuffs are known in the medical electronic field. In this type of conventional blood pressure meter, when a measuring time interval is shortened, fastening actions by the cuff are frequently repeated. As a result, heavy loads could be given to a human subject under examination, and internal hemorrhages may happen to occur in a human body portion around which the cuff is wound in the worst case.

In contrast to this type of blood pressure meters, there is another type of blood pressure meter capable of measuring only a variation in blood pressure, which does not directly measure an absolute value of blood pressure. For example, while this type of blood pressure meter grasps speeds at which pulse waves are propagated through an artery (pulse wave propagation speeds) and also grasps feature amounts of pulse waveforms to thereby constitute parameters thereof, a change amount thereof is converted into a change amount in blood pressure and then the blood pressure meter displays this converted blood pressure amount. Since this sort of blood pressure meter needs not repeat fastening actions by the cuff, no heavy load is given to the human subject under examination. Also, since this blood pressure meter can calculate in principle the blood pressure in response to one cardiac beat of ECG and pulse wave signals, blood pressure measurement can be carried out continuously under noninvasive condition.

However, the above-explained blood pressure meter, namely the blood pressure meter capable of measuring only the blood pressure variation, calculates the blood pressure based upon the change amount in the pulse waves. Therefore, if the outer disturbance is superimposed on the pulse waveforms due to the body movement (motion of living body), then this blood pressure meter owns such a problem that blood pressure measurement cannot be carried out correctly.

To solve this problem, the below-mentioned conventional techniques have been proposed.

(1) Japanese Patent No. 2664983 discloses a vital signal detecting apparatus having judgment means for determining as to whether or not body movement noise is produced. In the case that this judgment means judges the production of such body movement noise, lowering of the blood pressure measuring precision, which is caused by reading the body movement noise, can be prevented by such a manner that reading operation of sensor signals is interrupted for a predetermined time duration.

(2) Japanese Laid-open Patent Application No. 5-184547 describes a method for calculating a basic period of a present pulse wave by utilizing periods of plural pulse waves, and for correcting the amplitude of an abnormal pulse wave in response to fluctuation of the pulse wave period that is calculated from this basic period.

(3) A document of "Comparison on relationship between pulse wave propagation time and blood pressure of different measuring portions" (Japanese ME institute No. 38, Sendai, 21 to 23 April, 1999, page 373) describes a method capable of removing outer disturbance caused by the body movement from the pulse waves of the human body. In other words, this method is capable of removing adverse influences of general artifacts containing the body movement, from the pulse waves and the electrocardiogram. Concretely, while observing the 64 cardiac beats of the pulse waves appeared in the past from the monitoring time of the pulse waves, a portion having large dispersion of the pulse wave amplitude is removed, and the signal portions other than this removed portion are used for the analysis purpose.

However, the conventional method of the above-explained item (1) is not properly applied to such a blood pressure measurement under free action, in which the body movement noise is frequently superimposed on the vital signal.

The conventional method of the above-explained item (2) may be utilized as to a single abnormal pulse wave. However, this method can hardly calculate the basic frequency of the pulse wave under free action in which the pulse wave is frequently disturbed. Similarly to the conventional method of the item (1), this method of the item (2) is not suitable for the blood pressure measurement under free action.

In accordance with the conventional method of the above-explained item (3), since the signal portion on which the outer disturbance caused by the body movement is superimposed is not used, there is a limitation in the vital signal that can be used in the analysis. Also, the temporal continuity of the vital signal would be lost. In addition, when the outer disturbance caused by the body movement is applied for a long time duration, the resulting vital signal cannot be analyzed.

As a result, as to the noninvasive blood pressure meter adopting the system for measuring only the blood pressure variation, in such a case that the pulse waveforms are largely disturbed due to the body movement that is frequently produced under free action, the sufficiently high accuracy of predicting the blood pressure cannot be secured.

SUMMARY OF THE INVENTION

The present invention has been made in view of the above problems. An object of the present invention is to provide a vital signal detecting apparatus capable of detecting a vital signal, containing no outer disturbance, from pulse waves, and also capable of maintaining temporal continuity of the vital signal. Another object of the present invention is to provide a noninvasive blood pressure meter adopting a system of measuring only a blood pressure variation, and capable of measuring blood pressure continuously and precisely even under free action by separating noise, caused by body movement, from pulse wave components synchronized with cardiac beats.

According to the present invention, a vital signal detecting apparatus has at least two sensors for detecting first pulse waves and outputting analog signals corresponding to the first pulse waves; an A/D converter for converting the analog signals derived from the sensors into digital signals; a separation matrix calculation means for calculating a separation matrix for separating an outer disturbance caused by body movement, from the first pulse waves by utilizing statistic independency of a second pulse wave containing no outer disturbance and the outer disturbance; and a signal separation calculation means for separately deriving a vital signal corresponding to the second pulse wave and a body movement signal indicating the outer disturbance by operating the separation matrix with respect to the digital signals. Accordingly, the vital signal containing no outer disturbance can be detected from pulse waves continuously.

Specifically, the separation matrix calculation means can calculate the separation matrix in a case where it is considered that each of the first pulse waves detected by the sensors contains the outer disturbance and the second pulse wave containing no outer disturbance, and only amplitude is changed until the sensors detect the first pulse waves. Otherwise, the separation matrix calculation means can calculate the separation matrix in a case where it is considered that each of the first pulse waves detected by the sensors contains the outer disturbance caused by body movement and the second pulse wave containing no outer disturbance, and both frequency and phase thereof are changed linearly until the sensors detect the first pulse waves.

BRIEF DESCRIPTION OF THE DRAWINGS

Other objects and features of the present invention will become more readily apparent from a better understanding of the preferred embodiments described below with reference to the following drawings, in which.

DETAILED DESCRIPTION OF THE PREFERRED EMBODIMENTS

A principle action of the present invention is briefly explained first.

When outer disturbance caused by body movement is contained in pulse waves detected by sensors, the following cases may be conceived. That is, there is a case where it is considered that only amplitude is changed until the sensors detect the pulse waves containing the outer disturbance, and the outer disturbance is mixed with (superimposed on) pulse waves containing no outer disturbance. Also, there is another case where pulse waves are processed by a linear system, both frequencies and phases thereof are changed, and accordingly it is considered that outer disturbance caused by the body movement is mixed with the pulse waves containing no outer disturbance.

In such a case that plural signals which are statistically independent from each other are mixed with each other in an additive manner only by changing the amplitudes thereof, and also in the case that such plural signals are processed by the linear system and then the linear-processed signals are added to each other in the additive manner, it is in principle possible to recover the original signals by way of the following manner. That is, an inverse matrix of the pulse waves detected by the sensors is predicted from an algorithm capable of predicting the inverse matrix, and thereafter, this predicted inverse matrix is operated with respect to the pulse waves. This algorithm is described in detail in, for example, "An information-maximization approach to blind separation and blind deconvolution," Anthony I. Bell and Terrence J. Sejnowsky, Technical Report No. INC.9501, February 1995, Institute for Neural Computation, UCSD, San Diego, Calif. 92093-0523.

Accordingly, in the case that two sensors are employed, assuming now that a pulse wave (vital signal) to which no body movement is applied is represented as $s1(n)$; outer disturbance caused by body movement (body movement signal) is represented as $s2(n)$; and sensor signals are represented as $x1(n)$ and $x2(n)$ (note that symbol "n" indicates index of digital signal, i.e., n=0, 1, 2, 3, ...) when only the amplitudes thereof are changed to be added, the resulting sensor signals $x1(n)$ and $x2(n)$ may be expressed as follows:

$$x1(n) = a_{11} \times s1(n) + a_{12} \times s2(n) \qquad \ldots (1)$$

$$x2(n) = a_{21} \times s1(n) + a_{22} \times s2(n) \qquad \ldots (2)$$

On the other hand, when the sensor signals are processed by the linear system and the linear-processed sensor signals are added to each other, the resulting sensor signals $x1(n)$ and $x2(n)$ may be expressed as follows:

$$\begin{aligned} x1(n) = &\, a_{0,11} \times s1(n) + a_{0,12} \times s2(n) + a_{1,11} \times s1(n-1) + \\ &\, a_{1,12} \times s2(n-1) + \ldots + a_{L,11} \times s1(n-L) + \\ &\, a_{L,12} \times s2(n-L) \end{aligned} \qquad (3)$$

$$\begin{aligned} x2(n) = &\, a_{0,21} \times s1(n) + a_{0,22} \times s2(n) + a_{1,21} \times s1(n-1) + \\ &\, a_{1,22} \times s2(n-1) + \ldots + a_{L,21} \times s1(n-L) + \\ &\, a_{L,22} \times s2(n-L) \end{aligned} \qquad (4)$$

It should be noted that symbol "L" denotes a positive integer larger than, or equal to 1.

In both the above-explained cases (1) and (2), if an inverse matrix of a matrix "A" ($A_{11}=a_{11}$, $A_{12}=a_{12}$, $A_{21}=a_{21}$, $A_{22}=a_{22}$) is operated to $\{x1(n), x2(n)\}^t$ (symbol "t" being transpose), then both a vital signal including no body movement and a body movement signal can be obtained.

Also, in the above-described cases (3) and (4), an inverse filter matrix of a filter matrix may that is determined based upon a matrix $A_0$ ($A_{011}=a_{1,11}$, $A_{012}=a_{0,12}$, $A_{021}=a_{0,21}$, $A_{022}=a_{0,22}$), $A_1$ ($A_{111}=a_{1,11}$, $A_{112}=a_{1,12}$, $A_{121}=a_{1,21}$, $A_{122}=a_{1,22}$), ..., $A_1$ ($A_{L11}=a_{L,11}$, $A_{L12}=a_{L,12}$, $A_{L21}=a_{L,21}$, $A_{L22}=a_{L,22}$) may be operated. The inverse filter matrix is composed of two or more matrixes.

It should be understood that when the inverse matrix is predicted, such a non-linear function as $g(x)=1/\{1+\exp(-x)\}$ is used. A function, which is obtained by differentiating this non-linear function, is made coincident with a probability density function of a desirable vital signal, which is the most favorable function as viewed from a view point of a signal separation. However, even when the non-linear function such as $g(x)=1/\{1+\exp(-x)\}$ is employed, the signal separation can be achieved.

Based upon the above-explained operations, if it is possible to acquire such a pulse wave signal which is synchronized with cardiac beats and contains no outer disturbance component caused by the body movement, then the blood pressure can be predicted in a continuous manner from the feature change in the pulse waves in accordance with, for example, the below-mentioned method:

(a) A method for calculating blood pressure from a waveform change in pulse waves, while utilizing such a fact that the waveforms of the pulse waves in a portion under measurement may depend upon blood pressure values based upon cardiac beats.

(b) On the side of a peripheral blood vessel, a propagation time instant of a pulse wave may produce a delay, as compared with a cardiac beat (pulse wave propagation time). A pulse wave propagation speed with respect to pulse wave propagation time of a constant distance is expressed as a function of a volume elastic modulus of a blood vessel. When blood pressure is increased, the volume elastic modulus of the blood vessel is increased, and the wall of the blood vessel is hardened. Accordingly, the propagation speed is increased. As a result, if such a pulse wave signal synchronized with the cardiac beat can be obtained which does not contain the outer disturbance component caused by the body movement, the blood pressure change can be calculated from the pulse wave propagation time.

Then, referring to drawings, vital signal detecting apparatuses according to various preferred embodiments of the present invention will now be described specifically below.

[First Embodiment]

Figure 1:
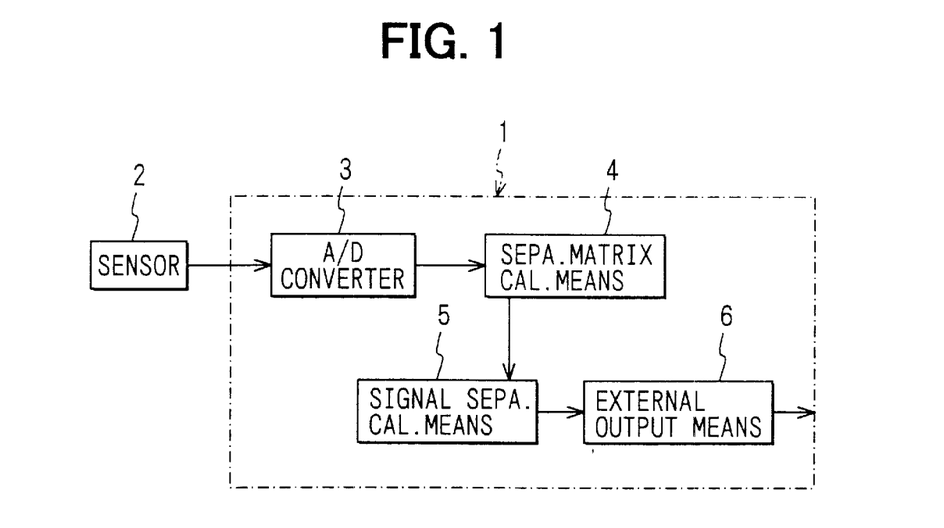
FIG. 1 is a block diagram showing a constitution of a vital signal detecting apparatus in a first preferred embodiment.

Referring first to FIG. 1, a vital signal detecting apparatus 1 according to a first embodiment corresponds to an apparatus for separating outer disturbance caused by body movement from pulse waves, which are detected by two sensors 2, and for thereby outputting a vital signal containing no outer disturbance. The vital signal detecting apparatus 1 is composed of an A/D converter 3, a separation matrix calculation means 4, a signal separation calculation means 5, and an external output means 6, which will be explained in detail.

The sensors 2 measure pulse waves of a human body as vital information, and correspond to, for example, well-known optical type pulse wave sensors equipped with a light-emitting element and a light-receiving element. The sensors 2 are attached to, for example, a finger of the human body. When light is irradiated from the light-emitting element toward the finger, the irradiated light is projected onto an arterial capillary that passes through an interior portion of the finger, and then is partially absorbed by hemoglobin contained in blood flowing through the arterial capillary. The remaining light is reflected from the arterial capillary to be scattered, and a part of the scattered light enters the light-receiving element.

At this time, since the amount of hemoglobin is changed in a wave manner by the pulse moves of blood, the amount of light, which is absorbed by the hemoglobin, is also changed in a wave manner. As a result, the amount of received light, which is reflected by the arterial capillary and then received by the light-receiving element, is varied. A change in this amount of received light is outputted to the A/D converter 3 as pulse wave information (for example, as voltage signals).

The A/D converter 3 inputs therein the sensor signals derived from the two sensors 2, and converts analog signals into digital signals $x1(n)$, $x2(n)$ ($n=0, 1, 2, \ldots$) at a sampling frequency of, for example, 100 Hz. Then, the A/D converter 3 supplies these digital signals to the separation matrix calculation means 4.

The separation matrix calculation means 4 contains a CPU and a memory. This separation matrix calculation means 4 corrects a 2×2 separation matrix $W(n)$ stored in the memory at the present time by only $\Delta W(n)$, while using the digital signals $x1(n)$ and $x2(n)$ supplied from the A/D converter 3 at the present time, and updates the values saved in the memory as $W(n+1)=W(n)+\Delta W(n)$. It should be noted that at such a time instant when this vital signal detecting apparatus is started, a value $W(0)$ of the memory is set in a unit matrix of 2×2.

The correction value $\Delta W(n)$ of the 2×2 separation matrix may be calculated in accordance with the below-mentioned formula:

$$\Delta W(n)=[W(n)^t]^{-1}+[I-2\times g\{W(n)\times x(n)\}]\times x(n)^t g(x)=1/\{1+\exp(-x)\}$$

Note that $x(n)=\{x1(n), x2(n)\}^t$ (t:transpose); symbol "I" shows a two-dimensional vector, which uses using 1 as a component, $I=\{1, 1\}^t$.

An inverse matrix of the matrix $W(n)^t$ may be calculated based upon a standard numeral value calculation method such as, for example, the LU resolving method (refer to "Numeral Value Calculating Method" written by H. NAGASHIMA published by SAKAKI book store). The value of the function "g" may also be calculated by the numeral value calculating method. The separation matrix $W(n+1)$ at a certain time, which has been corrected in the above-explained manner, is stored into the memory instead of the separation matrix $W(n)$ obtained immediately before it. Simultaneously, both the former separation matrix $W(n)$ and the digital signal $x(n)$ converted by the A/D converter 3 are supplied to the signal separation calculation means 5.

The signal separation calculation means 5 includes a CPU and a memory. This signal separation calculation means 5 calculates a vector, $y(n)=\{y1(n), y2(n)\}^t$, composed of a vital signal separated from body movement and also a body movement signal indicative of outer disturbance caused by the body movement, in accordance with such a manner that a product made between the separation matrix $W(n)$ and the digital signal $x(n)$, which are supplied from the separation matrix calculation means 4, is added to each other from the past time. Thereafter, the signal separation calculation means 5 supplies this calculated vector to the external output means 6.

The external output means 6 corresponds to a monitor apparatus, which outputs both the vital signal from which the outer disturbance caused by the body movement has been separated and also the body movement signal to an external appliance in synchronism with the sampling frequency of 100 Hz.

As explained above, even in such a case that the outer disturbance caused by the body movement is superimposed on the pulse waves detected by the sensors 2, if it is conceived that only the amplitudes are changed until the pulse waves containing this outer disturbance are detected by the sensors 2 and thus the outer disturbance caused by the body movement is mixed with such pulse waves containing no outer disturbance, the outer disturbance can be separated from the pulse waves by using one separation matrix calculated by the separation matrix calculation means 4.

When it is so conceived that since both the frequency and the phase are changed in a linear manner until the pulse waves containing the outer disturbance are detected by the sensors 2 and the outer disturbance caused by the body movement is mixed with the pulse waves containing no outer disturbance, the separation matrix calculation means 4 calculates two or more separation matrixes, and can separate the outer disturbance from the pulse waves by employing these two or more separation matrixes.

[Second Embodiment]

Figure 2:
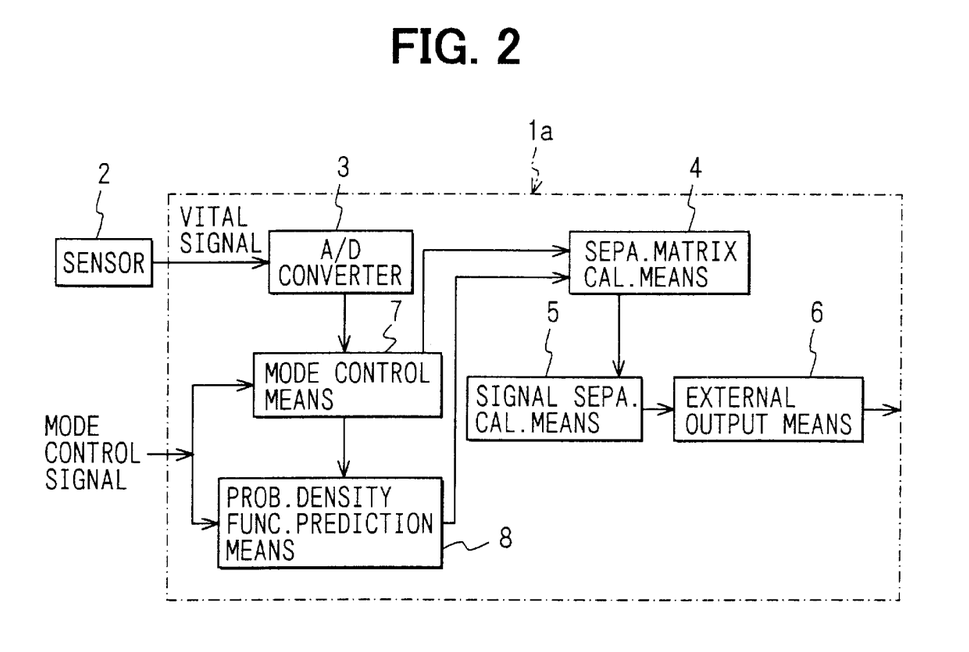
FIG. 2 is a block diagram showing a constitution of a vital signal detecting apparatus in a second preferred embodiment.

FIG. 2 is a schematic block diagram showing an arrangement of a vital signal detecting apparatus 1 according to a second embodiment of the present invention.

This vital signal detecting apparatus 1a has a mode control means 7 and a signal probability density function prediction means 8 in addition to the above-explained constitution of the first embodiment. The mode control means 7 switches outputs derived from the A/D converter 3 in response to the below-mentioned setting modes. The signal probability density function prediction means 8 predicts a probability density function (histogram) of pulse waves containing no outer disturbance caused by body movement.

As the setting mode, there are two setting modes, namely, a training mode and a separating mode, which are selectable by, for example, manipulating an external button. When any one of these setting modes is selected, a mode control signal (training mode signal or separating mode signal) is outputted in response to the selected mode. It should also be noted that the training mode is carried out under such a condition that a human subject under examination is kept stationary (namely, no body movement condition).

The mode control means 7 corresponds to a body movement judgment means according to the present invention. Upon receipt of the training mode signal, the mode control means 7 supplies the output of the A/D converter 3 to the signal probability density function prediction means 8. Upon receipt of the separation mode signal, the mode control means 7 supplies the output of the A/D converter 3 to the separation matrix calculation means 4.

The signal probability density function prediction means 8 contains a CPU and a memory. This signal probability density function prediction means 8 produces a histogram of digital signals, for example, a histogram of the amplitudes of the digital signal $x1(n)$, which are sequentially supplied from the A/D converter 3 in the training mode. This histogram is produced in accordance with the following manner.

That is, while a section between a maximum amplitude M available from the digital signal $x1(n)$ and a minimum amplitude m available from this digital signal $x1(n)$ is subdivided by, for example, 100, when the amplitude of the digital signal $x1(n)$ is entered into a certain subsection, the counter of this subdivided section is increased by 1. This histogram producing operation is carried out until the mode control signal is changed into the separation mode signal. When the setting mode is changed from the training mode into the separation mode, the signal probability density function prediction means 8 supplies the predicted histogram (function approximated to a line graph) to the separation matrix calculation means 4.

In the separation matrix calculation means 4, as the function g in the first embodiment, such a function is used, which is obtained by integrating the histogram (function approximated to the line graph) supplied from the signal probability density function prediction means 8.

Other operations of this vital signal detecting apparatus according to the second embodiment are similar to those of the first embodiment.

In the vital signal detecting apparatus of this second embodiment, the histogram is produced from the pulse waves that are detected under such a condition that the human subject under examination is kept stationary. Then, since the separation matrix is calculated by using this histogram, the outer disturbance caused by the body movement can be highly precisely separated from the vital signal.

It should be understood that the vital signal detecting apparatus according to this embodiment may be apparently applied to any of the below-mentioned two cases, namely one case where it is so conceived that only the amplitudes are changed until the pulse waves containing the outer disturbance are detected by the sensors 2 and thus the outer disturbance caused by the body movement is mixed with such pulse waves containing no outer disturbance, and the other case where it is so conceived that both the frequency and the phase are changed in a linear manner until the pulse waves containing the outer disturbance are detected by the sensors 2, and the outer disturbance caused by the body movement is mixed with the pulse waves containing no outer disturbance.

[Third Embodiment]

Figure 3:
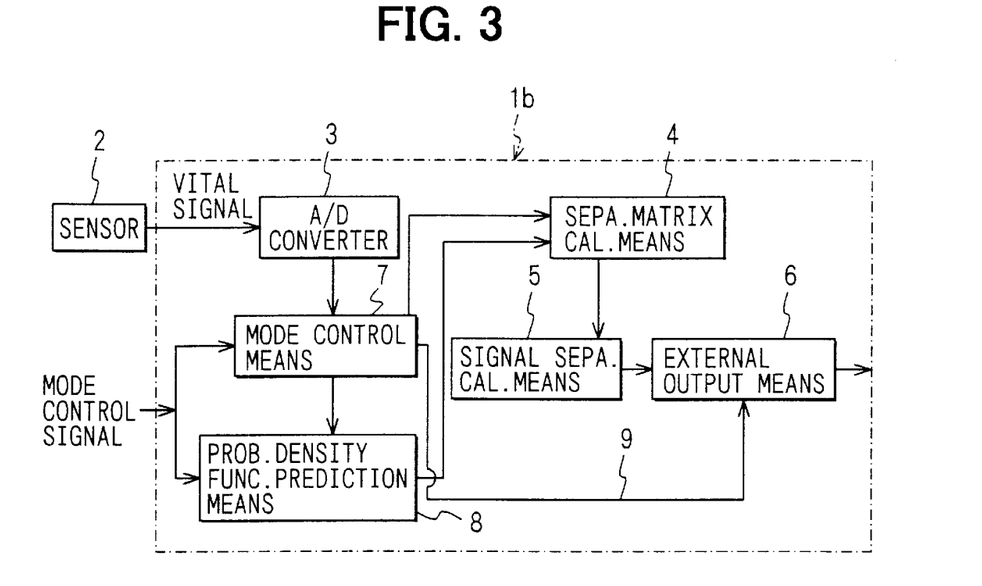
FIG. 3 is a block diagram showing a constitution of a vital signal detecting apparatus in a third preferred embodiment.

FIG. 3 is a schematic block diagram showing an arrangement of a vital signal detecting apparatus 1b according to a third embodiment of the present invention.

This vital signal detecting apparatus 1b has a bypass signal circuit (signal bypass means) 9 in addition to the above-explained constitution of the second embodiment 9. That is, when the training mode is selected, namely, when the training mode signal is entered into the mode control means 7, since the human subject under examination is in the stationary state, outer disturbances caused by the body movement are not basically applied. As a consequence, as shown in FIG. 3, when the training mode is selected, the output signal of the A/D converter 3 may be directly supplied from the mode control means 7 via the bypass signal circuit 9 to the external output means 6.

[Fourth Embodiment]

Figure 4:
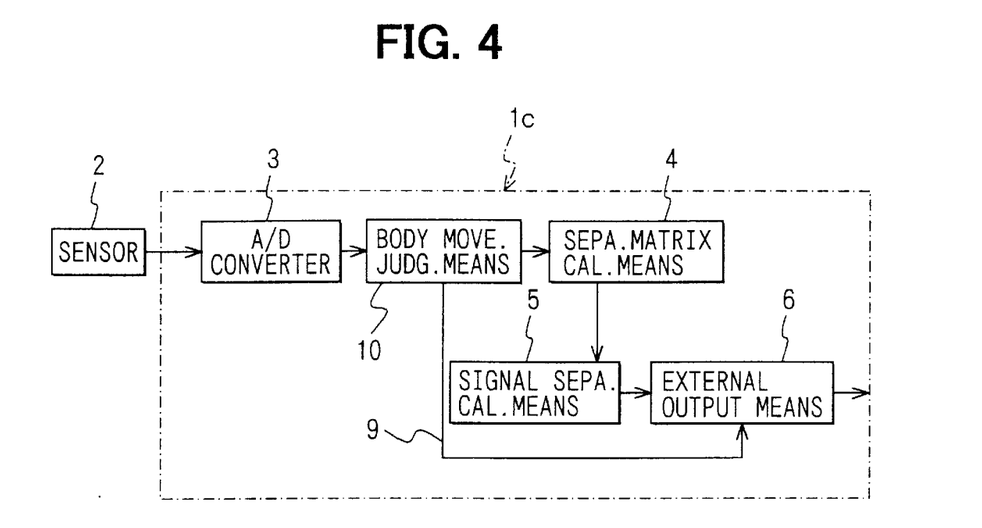
FIG. 4 is a block diagram showing a constitution of a vital signal detecting apparatus in a fourth preferred embodiment.

FIG. 4 is a schematic block diagram showing an arrangement of a vital signal detecting apparatus 1c according to a fourth embodiment of the present invention.

This vital signal detecting apparatus 1c has a body movement judgment means 10, and a bypass signal circuit 9 in addition to the above-explained constitution of the first embodiment. The body movement judgment means 10 judges as to whether or not outer disturbance caused by body movement is contained in pulse waves detected by the sensors 2. When this body movement judgment means 10 judges that the outer disturbance caused by the body movement is not contained in the pulse waves detected from the sensors 2, the output derived from the A/D converter 3 is directly supplied from the body movement judgment means 10 via the bypass signal circuit 9 to the external output means 6.

In this case, as the body movement judgment means 10, for example, an acceleration speed sensor capable of sensing as to whether or not body movement is present may be employed. Alternatively, as explained with respect to the second embodiment, a signal detecting means capable of detecting the signal (the training mode signal in the second embodiment) outputted when the human subject under examination is in the stationary condition may be provided.

Next, noninvasive blood pressure meters according to variously preferred embodiments of the present invention will now be described with reference to drawings.

[Fifth Embodiment]

Figure 5:
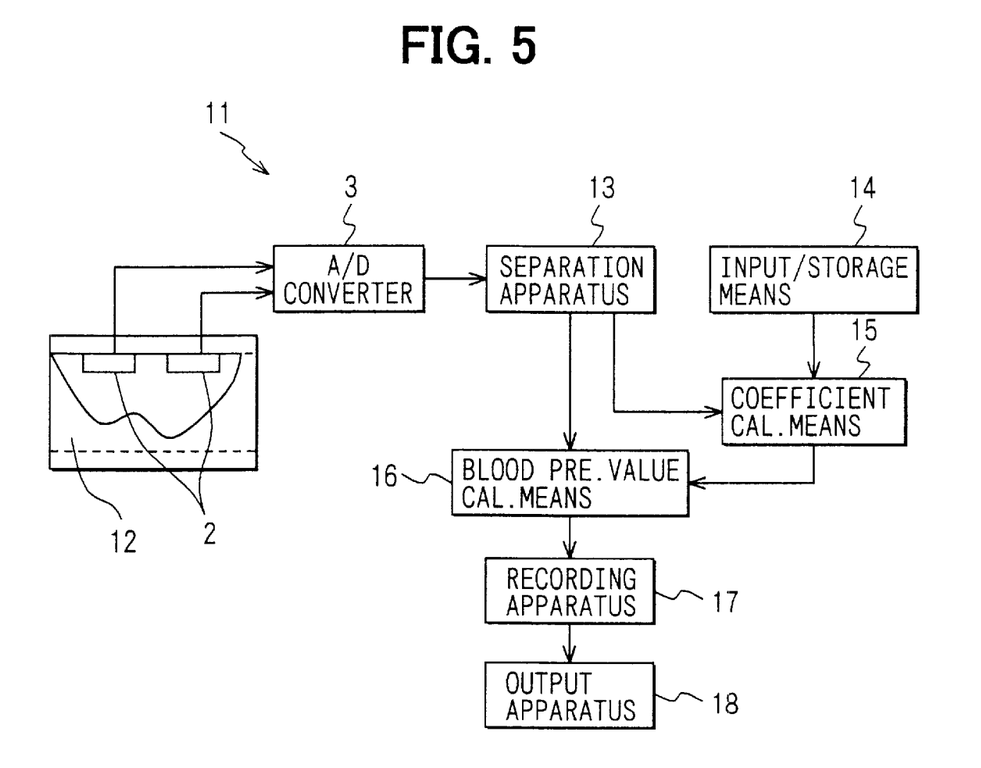
FIG. 5 is a block diagram showing a constitution of a noninvasive blood pressure meter in a fifth preferred embodiment.

FIG. 5 is a schematic block diagram indicating an arrangement of a noninvasive blood pressure meter 11 according to a fifth embodiment of the present invention.

As indicated in FIG. 5, the noninvasive blood pressure meter 11 is composed of two sets of sensors 2, a cuff 12, an A/D converter 3, an outer disturbance separation apparatus 13 (discussed later), an input/storage means 14, a coefficient calculation means 15, a blood pressure value calculation means 16, a recording apparatus 17, and an output apparatus 18.

The sensors 2 detect pulse waves of a human subject under examination. The cuff 12 holds the two sensors 2 under constant pressure. The A/D converter 3 converts a sensor signal (analog signal) into a digital signal corresponding thereto. The outer disturbance separation apparatus 13 separates outer disturbance caused by body movement from a digital sensor signal. The input/storage means 14 inputs/stores therein a blood pressure value of the subject under examination as a reference blood pressure value, which is separately measured.

The coefficient calculation means calculates a coefficient for making a pulse wave signal, which is synchronized with a cardiac beat containing no outer disturbance, correspond to the reference blood pressure value. The blood pressure value calculation means 16 continuously calculates a blood pressure value from both the calculated coefficient and the pulse wave signal synchronized with the cardiac beat containing no outer disturbance. The recording apparatus 17 records thereon the continuous blood pressure values calculated by the blood pressure value calculation means 16. The output apparatus 18 outputs the calculated continuous blood pressure to an external appliance.

The sensors 2 are, for example, the optical type pulse wave sensor as explained in the above-described vital signal detecting apparatus 1. These sensors 2 are held by the cuff 12 in such a manner that these sensors 2 are closely fitted to an arm, or another portion of the human subject under examination. An amplifier (not shown) may amplify the sensor output signal, and it is so assumed that both the sensors 2 and the amplifier have better linear characteristics.

Also, it is desirable that the sensor outputs satisfy the mutually united requirements to perform the outer distance separation process under better condition. In other words, in the case where the positions of the plural sensors 2 are excessively separated from each other, the different outer distance factors dominantly appear only in one sensor output, by which the blood pressure calculating precision would be lowered. As an extreme case, in a case where the respective two sensors are arranged on a tip portion of a right arm of an object under examination and a tip portion of a left arm thereof and only the right arm is lightly swung, the adverse influence of the body movement is largely given to the sensor 2 which is mounted on the right arm, whereas the adverse influence of the body movement can be hardly given to the sensor 2 which is mounted on the left arm. Therefore, the respective sensors 2 are preferably disposed in such a manner that the pulse waves in the same blood vessel system can be measured, in which the same outer disturbance factor may be easily superimposed on the signals For example, in such a case where while a center of one sensor 2 is separated from another center of another sensor 2 along an arm length direction of the subject under examination by 3 cm the arms are lightly swung, there arises a shift in the phases of the sensor outputs. However, as to the outer disturbance caused by the body movement, such waveforms made clearly coincident with each other can be obtained. In other words, with respect to the waveform shapes, the united characteristic can be established. Also, in such a case that while a center of one sensor 2 is separated from another center of another sensor 2 along an arm circumferential direction of an object under examination by 3 cm the arms are lightly swung, although the phases of the sensor outputs are clearly made coincident with each other, there arises a very small difference in the amplitudes of the outer disturbance. In this case, as to the mutual phases, the united characteristic can be obtained.

The cuff 12 can hold the two sensors 2 under a constant pressure (for example, 20 mmHg) that is lower than diastolic pressure of the human subject under examination.

The A/D converter 3 inputs therein the sensor signals derived from the two sensors 2, and converts analog signals into digital signals $x1(n)$, $x2(n)$ ($n=0, 1, 2, \ldots$) at a sampling frequency of, for example, 100 Hz. Then, the A/D converter 3 supplies these digital signals to the outer disturbance separation apparatus 13.

The outer disturbance separation apparatus 13 is an apparatus capable of separating outer disturbance $y2(n)$ $\{\approx s2(n)\}$ caused by the body movement from the signals $x1(n)$ and $x2(n)$, which are digitally converted by the A/D converter 3, and also capable of recovering a pulse wave signal $y1(n)$ $\{\approx s1(n)\}$ formed based upon the cardiac beats containing no outer disturbance.

Figure 6:
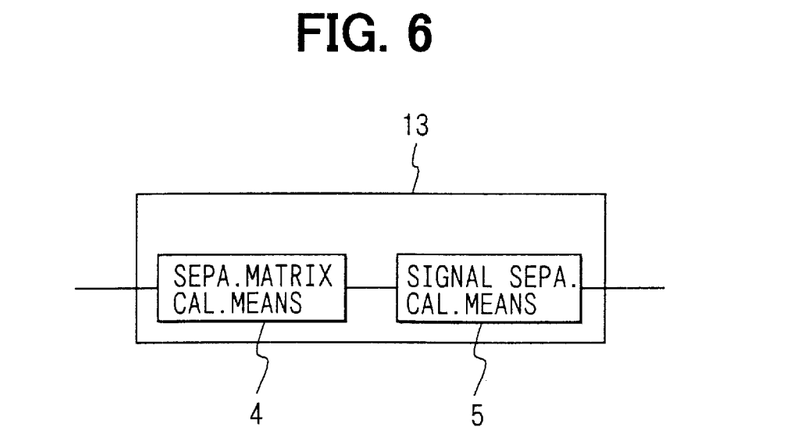
FIG. 6 is a block diagram showing an outer disturbance separation apparatus in the fifth embodiment.

As indicated in FIG. 6, this outer disturbance separation apparatus 13 is constituted by a separation matrix calculation means 4 and a signal separation calculation means 5. Since functions and operations of both the separation matrix calculation means 4 and the signal separation calculation means 5 are substantially identical to those of the above-explained vital signal detecting apparatus 1, descriptions thereof are omitted.

Next, operations of the noninvasive blood pressure meter 11 will be explained below.

The continuous blood pressure value is calculated based upon the pulse wave signal $y1(n)$ formed based on the cardiac beats and recovered by the outer disturbance separation apparatus 13, in accordance with the following manner.

Figure 7:
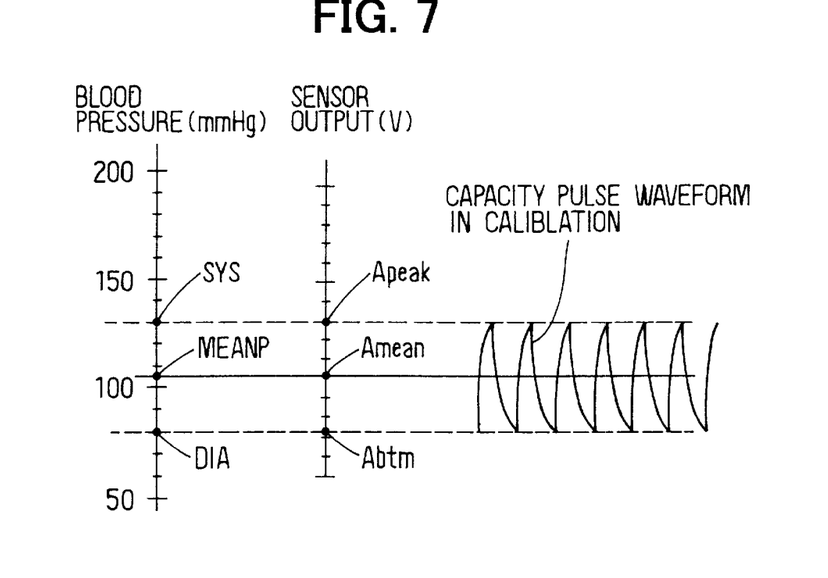
FIG. 7 is an explanatory view showing a method for measuring a blood pressure in the fifth embodiment.

First, the coefficient calculation means 15 samples the separated pulse wave signal $y1(n)$ for, for example, 10 cardiac beats, and then additive-averages the sampled pulse wave signals so as to synthesize a reference pulse wave "A." An average value "Amean" is calculated from this reference pulse wave "A" by averaging a peak value "Apeak", a bottom value "Abtm" and a DC component (see FIG. 7).

Separately, systolic pressure "SYS", diastolic pressure "DIA", and average arterial pressure "MEANP" of a human subject under examination are measured, and then, the measured values are input/recorded as reference values for calibration (namely, as reference blood pressure values).

Next, a calculation is carried out to obtain a coefficient "C" used to establish a relationship between a difference between the peak value Apeak and the bottom value Abtm, and another difference between the systolic pressure SYS and the diastolic pressure DIA.

Subsequently, the blood pressure value calculation means 16 can calculate the continuous blood pressure value "BP" from the digital value $y1(t)$ of the pulse wave at the present time by employing the below-mentioned formula:

$$BP = \{y1(t) - Amean\} \times C + MEANP$$

It should be noted that the digital values $y1(t)$ of the pulse waves are acquired time to time, from which the body movement is separated. The calculated continuous blood pressure value BP is recorded on the recording apparatus 17, and is outputted from the output apparatus 18 to the external appliance, if required.

[Sixth Embodiment]

Figure 8:
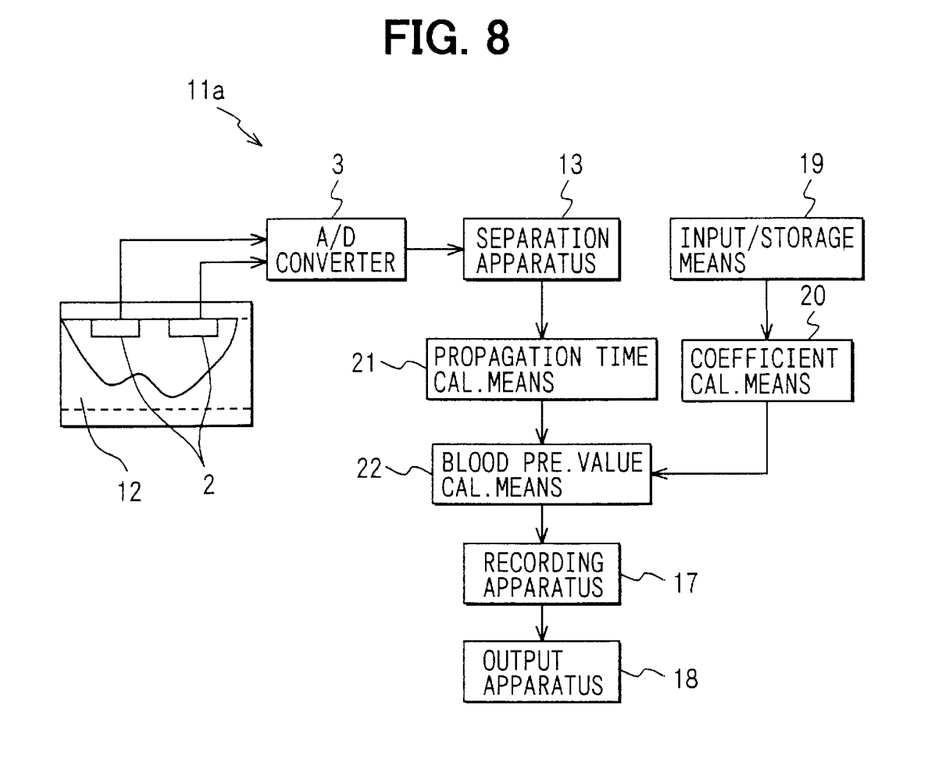
FIG. 8 is a block diagram showing a constitution of a noninvasive blood pressure meter in a sixth preferred embodiment.

FIG. 8 is a schematic block diagram indicating an arrangement of a noninvasive blood pressure meter 11a according to a sixth embodiment of the present invention.

As indicated in FIG. 8, the noninvasive blood pressure meter 11a is composed of two sensors 2, a cuff 12, an A/D converter 3, an outer disturbance separation apparatus 13, an input/storage means 19, a coefficient calculation means 20, a pulse wave propagation time calculation means 21, a blood pressure value calculation means 22, a recording apparatus 17, and an output apparatus 18.

The sensors 2 detect pulse waves of a human subject under examination. The cuff 12 holds the two sensors 2 under constant pressure. The A/D converter 3 converts a sensor signal (analog signal) into a digital signal corresponding thereto. The outer disturbance separation apparatus 13 separates outer disturbance caused by body movement from the digital sensor signal.

The input/storage means 19 inputs/stores therein both blood pressure values (systolic pressure and diastolic pressure) of the subject object under examination and pulse wave propagation time as reference values for calibration purposes, which are separately measured. This pulse wave propagation time corresponds to such propagation time of pulse wave components that are synchronized with cardiac beats containing no outer disturbance.

The coefficient calculation means 20 calculates a coefficient used to establish a correspondence relationship between the blood pressure value and the pulse wave propagation time based upon the reference values thereof (blood pressure value and pulse wave propagation time). The pulse wave propagation time calculation means 21 calculates pulse wave propagation time from the pulse wave signals based upon the cardiac beats and from which the outer disturbance is separated.

The blood pressure value calculation means 22 continuously calculates a blood pressure value based upon the calculated pulse wave propagation time and the calculated coefficient. The recording apparatus 17 records thereon the calculated continuous blood pressure, and the output apparatus 18 outputs the calculated continuous blood pressure to an external appliance.

Next, operations of the noninvasive blood pressure meter 11a will be explained below.

The operations up to the outer disturbance separation apparatus 13 in this noninvasive blood pressure meter 11a are substantially the same as those of the fifth embodiment. The continuous blood pressure value is calculated based upon the pulse wave signal y1(n), which is recovered by the outer disturbance separation apparatus 13 in response to the cardiac beat, in accordance with the following manner.

First, for example, pulse wave propagation time, systolic pressure, and diastolic pressure are separately measured when the subject under examination is under a stationary condition, and also is loaded by motion. Then, these measurement values are input into the input/storage means 19 as the reference values for calibration purposes.

Next, the coefficient calculation means 20 calculates a coefficient that is required to calculate a blood pressure value from the pulse wave propagation time. In other words, assuming now that the blood pressure values and the pulse wave propagation time when the respective reference values are measured are represented with "P1", "P2", "T1", "T2", and also different constants specific to subjects under examination are represented with "α", "β" the following formulas can be established:

$$P1 = \alpha \times T1 + \beta$$

$$P2 = \alpha \times T2 + \beta$$

When the specific constants α and β are calculated from the above-explained formulas, the pulse wave propagation time calculation means 21 calculates pulse wave propagation time T from pulse waveforms which are subsequently obtained time to time and from which the body movement is separated. Then, a continuous blood pressure value "BP" may be calculated by the blood pressure value calculation means 22:

$$BP = \alpha \times T + \beta$$

Figure 9:
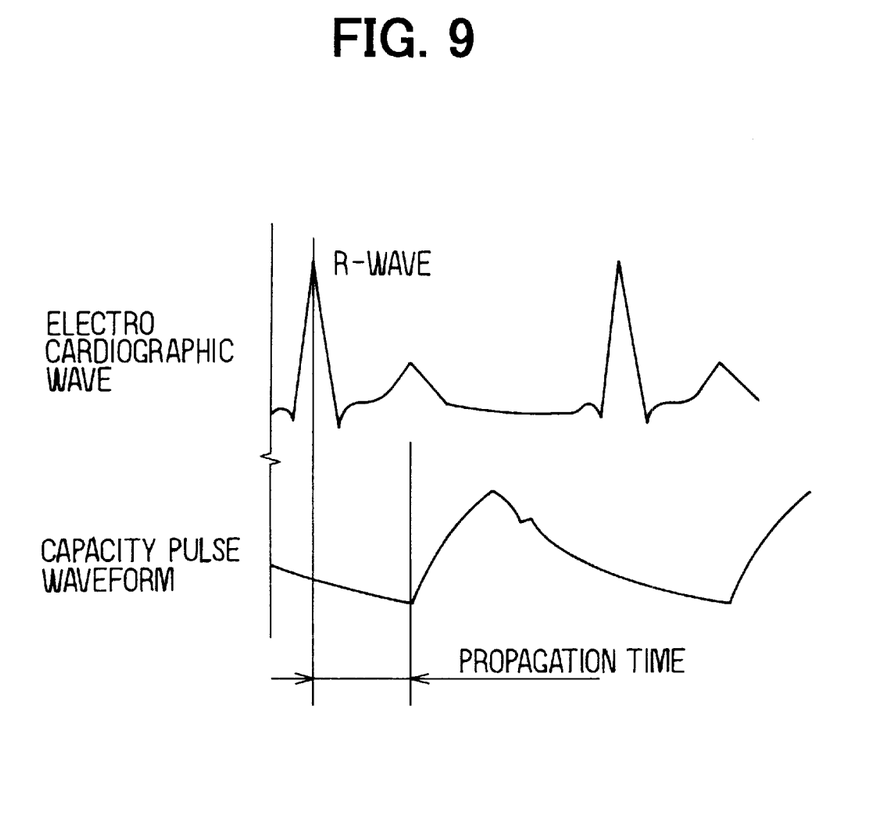
FIG. 9 is a graph showing a relation between an electrocardiographic wave and a pulse wave.

The calculated continuous blood pressure value BP is recorded on the recording apparatus 17, and is outputted from the output apparatus 18 to the external appliance, if necessary. It should be noted that when the pulse wave propagation time is calculated, for example, delay time of a specific point contained in a pulse wave may be calculated based upon an R-wave of an electrocardiographic wave that is measured by an electrocardiographic electrode (see FIG. 9).

In the noninvasive blood pressure meters 11, 11a as described in the fifth embodiment and the sixth embodiments, since the outer disturbance caused by the body movement can be separated from the pulse waves detected by the sensors 2 so as to derive the pulse wave components that are synchronized with the cardiac beats, the blood pressure can be continuously measured even under free action where the body movement frequently occurs. Also, since fastening action by the cuff 12 is no longer repeated, the continuous blood pressure measuring operation can be carried out under noninvasive condition without giving the heavy load to the subject under examination.

Furthermore, a mechanical apparatus such as a compressor required to control the cuff pressure is no longer needed, and also, the large and heavy electric components such as large capacity batteries used to drive this mechanical apparatus is no longer required. The noninvasive blood pressure meter of the present invention can be easily made compact and in light weight, and may be constituted as a portable blood pressure meter.

As apparently from foregoing descriptions, when the blood pressure value of the subject under examination is separately measured as the reference value for calibration purpose, the blood pressure value may be measured while using the cuff 12 that holds the sensors 2.

It should also be noted that the above-explained embodiments indicate that example in which the cuff 12 holds the sensors 2. However, the cuff 12 is not always used, but any other members may be employed, by which the sensors 2 may be held under such constant pressure lower than, or equal to diastolic pressure of a subject under examination. For example, a band made of rubber, a belt capable of adjusting holding force, or the like may be employed alternatively.

While the present invention has been shown and described with reference to the foregoing preferred embodiments, it will be apparent to those skilled in the art that changes in form and detail may be made therein without departing from the scope of the invention as defined in the appended claims.

What is claimed is:

1. A vital signal detecting apparatus comprising:
   at least two sensors for detecting first pulse waves and outputting analog signals corresponding to the first pulse waves;

an A/D converter for converting the analog signals derived from the sensors into digital signals;

a separation matrix calculation means for calculating a separation matrix in a case where it is considered that each of the first pulse waves detected by the sensors contains an outer disturbance caused by body movement and a second pulse wave containing no outer disturbance, and only amplitude is changed until the sensors detect the first pulse waves, the separation matrix being for separating the outer disturbance from the first pulse waves by utilizing statistic independency of the second pulse wave and the outer disturbance; and a signal separation calculation means for separately deriving a vital signal corresponding to the second pulse wave and a body movement signal indicating the outer disturbance by operating the separation matrix with respect to the digital signals.

2. The vital signal detecting apparatus according to claim 1, further comprising a signal output means for outputting the vital signal derived from the signal separation calculation means to an external appliance.

3. The vital signal detecting apparatus according to claim 1, further comprising:

a body movement judgment means for determining as to whether the first pulse waves derived from the sensors contain the outer disturbance caused by the body movement; and a signal bypass means for outputting the digital signals converted by the A/D converter, while bypassing the separation matrix calculation means and the signal separation calculation means when it is determined that the first pulse waves contain no outer disturbance.

4. The vital signal detecting apparatus according to claim 1, further comprising a probability density function prediction means for predicting a probability density function of the first pulse waves derived from the sensors when the first pulse waves contain no outer disturbance, wherein:

the separation matrix calculation means calculates the separation matrix by using the probability density function.

5. The vital signal detecting apparatus according to claim 4, further comprising a body movement judgment means for determining as to whether the first pulse waves derived from the sensors contain the outer disturbance, wherein:

the probability density function prediction means predicts the probability density function of the first pulse waves derived from the sensors when the body movement judgment means determines that the first pulse waves contain no outer disturbance caused by the body movement.

6. The vital signal detecting apparatus according to claim 5, further comprising a signal bypass means for outputting the digital signals converted by the A/D converter to an external appliance while bypassing the separation matrix calculation means and the signal separation calculation means when the body movement judgment means determines that the first pulse waves derived from the sensors contain no outer disturbance caused by the body movement.

7. A vital signal detecting apparatus comprising:

at least two sensors for detecting first pulse waves and outputting analog signals corresponding to the first pulse waves;

an A/D converter for converting the analog signals derived from the sensors into digital signals;

a separation matrix calculation means for calculating a plurality of separation matrixes in a case where it is considered that each of the first pulse waves detected by the sensors contains an outer disturbance caused by body movement and a second pulse wave containing no outer disturbance, and both frequency and phase thereof are changed linearly until the sensors detect the first pulse waves, the separation matrixes being for separating the outer disturbance from the first pulse waves by utilizing statistic independency of the second pulse wave and the outer disturbance; and a signal separation calculation means for separately deriving a vital signal corresponding to the second pulse wave and a body movement signal indicating the outer disturbance by operating the separation matrixes with respect to the digital signals.

8. The vital signal detecting apparatus according to claim 7, further comprising a signal output means for outputting the vital signal derived from the signal separation calculation means to an external appliance.

9. The vital signal detecting apparatus according to claim 7, further comprising:

a body movement judgment means for determining as to whether the first pulse waves derived from the sensors contain the outer disturbance caused by the body movement; and a signal bypass means for outputting the digital signals converted by the A/D converter, while bypassing the separation matrix calculation means an d the signal separation calculation means when it is determined that the first pulse waves contain no outer disturbance.

10. The vital signal detecting apparatus according to claim 7, further comprising a probability density function prediction means for predicting a probability density function of the first pulse waves derived from the sensors when the first pulse waves contain no outer disturbance, wherein:

the separation matrix calculation means calculates the separation matrixes by using the probability density function.

11. The vital signal detecting apparatus according to claim 10, further comprising a body movement judgment means for determining as to whether the first pulse waves derived from the sensors contain the outer disturbance, wherein:

the probability density function prediction means predicts the probability density function of the first pulse waves derived from the sensors when the body movement judgment means determines that the first pulse waves contain no outer disturbance caused by the body movement.

12. The vital signal detecting apparatus according to claim 11, further comprising a signal bypass means for outputting the digital signals converted by the A/D converter to an external appliance while bypassing the separation matrix calculation means and the signal separation calculation means when the body movement judgment means determines that the first pulse waves derived from the sensors contain no outer disturbance caused by the body movement.

13. A noninvasive blood pressure meter comprising:

at least two sensors for detecting first pulse waves when the sensors are held on a human body surface of a human subject under examination, and outputting the first pulse waves as analog signals;

an A/D converter for converting the analog signals derived from the sensors into digital signals;

a separation matrix calculation means for calculating a plurality of separation matrixes in a case where it is considered that each of the first pulse waves detected by the sensors contains an outer disturbance caused by body movement and a second pulse wave containing no outer disturbance, and both frequency and phase thereof are changed linearly until the sensors detect the first pulse wave, the plurality of separation matrixes being for separating the outer disturbance from the first pulse waves containing the outer disturbance by utilizing statistic independency of the second pulse wave containing no outer disturbance and the outer disturbance;

a signal separation calculation means for separately deriving the second pulse wave containing no outer disturbance and a body movement component indicating the outer disturbance, by operating the plurality of separation matrixes with respect to the digital signals; and a blood pressure calculation means for calculating a blood pressure value continuously based on the second pulse wave containing no outer disturbance derived from the signal separation calculation means.

14. The noninvasive blood pressure meter according to claim 13, further comprising:

an input/storage means for imputing and storing therein a blood pressure value of the human subject as a reference blood pressure that is detected separately from the first pulse waves; and a coefficient calculation means for calculating a coefficient for making the second pulse wave containing no outer disturbance, obtained by the signal separation calculation means, correspond to the reference blood pressure, wherein the blood pressure calculation means calculates the blood pressure value continuously based on the second pulse wave and the coefficient calculated by the coefficient calculation means.

15. The noninvasive blood pressure meter according to claim 13, further comprising:

an input/storage means for imputing and storing therein a blood pressure value of the human subject as a reference blood pressure and a propagation time of a pulse wave containing no outer disturbance as a reference pulse wave propagation time, the blood pressure value and the second pulse wave being detected separately from the first pulse waves;

a coefficient calculation means for calculating a coefficient that makes the reference blood pressure correspond to the reference pulse wave propagation time;

a pulse wave propagation time calculation means for calculating a propagation time of the second pulse wave obtained by the signal separation calculation means, wherein the blood pressure calculation means calculates the blood pressure value continuously based on the propagation time of the second pulse wave derived from the pulse wave propagation time calculation means and the coefficient calculated by the coefficient calculation means.

16. The noninvasive blood pressure meter according to claim 13, further comprising a cuff for being attached to the human body surface of the human subject, wherein the cuff holds the two sensors under a pressure that is lower than a diastolic pressure of the human subject.

17. The noninvasive blood pressure meter according to claim 13, wherein the two sensors are attached to positions where the first pulse waves are detected from an identical blood vessel system.

18. The noninvasive blood pressure meter according to claim 17, wherein the two sensors are disposed in a circumferential direction perpendicular to the identical blood vessel system.

19. The noninvasive blood pressure meter according to claim 13, wherein the two sensors are disposed along an identical blood vessel system linearly.

* * * * *